US011672470B2

(12) United States Patent
Kayser et al.

(10) Patent No.: US 11,672,470 B2
(45) Date of Patent: Jun. 13, 2023

(54) SYSTEMS AND METHODS FOR DETERMINING AN OBJECTIVE PRESSURE INJURY SCORE AND ALTERING A TREATMENT PLAN BASED ON THE SAME

(71) Applicant: Hill-Rom Services, Inc., Batesville, IN (US)

(72) Inventors: Susan Kayser, Batesville, IN (US); Timothy Receveur, Apex, NC (US); Bradley Smith, Raleigh, NC (US); Barry Brown, Sussex, WI (US); Charles Lachenbruch, Batesville, IN (US); Lance Shapiro, Mount Pleasant, SC (US)

(73) Assignee: Hill-Rom Services, Inc., Batesville, IN (US)

( * ) Notice: Subject to any disclaimer, the term of this patent is extended or adjusted under 35 U.S.C. 154(b) by 451 days.

(21) Appl. No.: 16/682,792

(22) Filed: Nov. 13, 2019

(65) Prior Publication Data

US 2020/0155059 A1    May 21, 2020

Related U.S. Application Data

(60) Provisional application No. 62/768,395, filed on Nov. 16, 2018.

(51) Int. Cl.
*A61B 5/00* (2006.01)
*A61G 7/05* (2006.01)
(Continued)

(52) U.S. Cl.
CPC .............. *A61B 5/447* (2013.01); *A61B 5/01* (2013.01); *A61B 5/0205* (2013.01);
(Continued)

(58) Field of Classification Search
CPC ......... A61B 5/447; A61B 5/01; A61B 5/0205; A61B 5/1114; A61B 5/6892;
(Continued)

(56) References Cited

U.S. PATENT DOCUMENTS 8,826,473 B2    9/2014  Flanagan et al.
9,220,455 B2 *  12/2015 Sarrafzadeh ........... A61B 5/447
(Continued)

FOREIGN PATENT DOCUMENTS

EP    2392303 A1    12/2011
EP    2508128 A1    10/2012
(Continued)

OTHER PUBLICATIONS

"Eunice Park-Lee, et al., Pressure Ulcers Among Nursing Home Residents: United States, 2004, 2009, CDC" (Year: 2009).*
(Continued)

*Primary Examiner* — Joseph M Dietrich
*Assistant Examiner* — Michael T. Holtzclaw
(74) *Attorney, Agent, or Firm* — Dinsmore & Shohl LLP (57) ABSTRACT

Systems include a plurality of sensors coupled to a person support apparatus, at least one moisture sensor configured to sense a moisture level between the person and the support surface, and at least one computing device coupled to the plurality of sensors coupled to the person support apparatus and the at least one moisture sensor. The at least one computing device receives data from the plurality of sensors coupled to the person support apparatus and the at least one moisture sensor, obtains data from an electronic medical record associated with the person supported by the person support apparatus, calculates a pressure injury score indicative of a likelihood that the person will develop a pressure injury based on the data from the plurality of sensors, the at least one moisture sensor, and the electronic medical record, and alters a treatment plan for the person based on the calculated pressure injury score.

9 Claims, 4 Drawing Sheets

(51) Int. Cl.
    *A61B 5/01*         (2006.01)
    *A61B 5/11*         (2006.01)
    *A61G 7/00*        (2006.01)
    *A61B 5/0205*     (2006.01)
    *A61B 5/021*      (2006.01)

(52) U.S. Cl.
    CPC .......... *A61B 5/1114* (2013.01); *A61B 5/6892* (2013.01); *A61B 5/7275* (2013.01); *A61G 7/001* (2013.01); *A61G 7/0527* (2016.11); *A61B 5/021* (2013.01); *A61B 2560/0247* (2013.01); *A61B 2562/0252* (2013.01)

(58) Field of Classification Search
    CPC .................. A61B 5/7275; A61B 5/021; A61B 2560/0247; A61B 2562/0247; A61B 2562/0252; A61B 5/6891; A61B 5/1115; A61B 5/1116; A61G 7/001; A61G 7/0527; A61G 2203/30; A61G 2203/42; A61G 7/057
    See application file for complete search history.

(56) References Cited

U.S. PATENT DOCUMENTS

| | | |
|---|---|---|
| 9,295,600 B2 | 3/2016 | Receveur |
| 2010/0312076 A1 | 12/2010 | Bly et al. |
| 2011/0083271 A1 | 4/2011 | Bhai |
| 2012/0259248 A1* | 10/2012 | Receveur .............. A61B 5/1118 |
| | | 600/595 |
| 2013/0249695 A1* | 9/2013 | Hann ..................... A61B 5/441 |
| | | 340/573.7 |
| 2013/0281804 A1* | 10/2013 | Lee ........................ A61G 7/057 |
| | | 600/324 |
| 2013/0317399 A1* | 11/2013 | Ribble ................... G16H 50/30 |
| | | 601/84 |
| 2014/0304915 A1 | 10/2014 | Lachenbruch |
| 2015/0371522 A1* | 12/2015 | Mravyan ............ A61G 7/05776 |
| | | 340/573.1 |
| 2017/0027498 A1* | 2/2017 | Larson ................... A61B 5/002 |
| 2017/0360357 A1* | 12/2017 | Larson .................. A61B 5/1115 |
| 2020/0405217 A1* | 12/2020 | Jayaraman ............. G08B 21/04 |
| 2021/0161462 A1* | 6/2021 | Lafleche ............... A61B 5/1116 |
| 2021/0361225 A1* | 11/2021 | Dunn ................... A61B 5/6833 |

FOREIGN PATENT DOCUMENTS

| | | | |
|---|---|---|---|
| EP | 2667313 A2 | 11/2013 | |
| WO | WO-2017218725 A1 * | 12/2017 | ........... A61B 5/1115 |
| WO | 2019199606 A2 | 10/2019 | |

OTHER PUBLICATIONS

Deng, et al. Predicting the Risk for Hospital-Acquired Pressure Ulcers in Critical Care Patients, CriticalCareNurse, vol. 37, No. 4., Aug. 2017, 12 pages.

Extended European Search Report for European Application No. 19208724.5 dated Mar. 30, 2020, 10 pages.

European Office Action for Appln. No. 19 208 724.5-1113, dated Jan. 13, 2022, 8 pages.

* cited by examiner

SYSTEMS AND METHODS FOR DETERMINING AN OBJECTIVE PRESSURE INJURY SCORE AND ALTERING A TREATMENT PLAN BASED ON THE SAME

CROSS-REFERENCE TO RELATED APPLICATIONS

The present application claims the benefit of and priority to U.S. Provisional Application No. 62/768,395, titled "Systems and Methods for Determining an Objective Pressure Injury Score and Altering a Treatment Plan Based on the Same," filed Nov. 16, 2018, the entire contents of which is hereby incorporated by reference.

TECHNICAL FIELD

The present specification generally relates to systems and methods for determining a likelihood that an individual will develop a pressure injury and, more particularly, to systems and methods for determining an objective pressure injury score indicative of a likelihood that an individual will develop a pressure injury.

BACKGROUND

In order to prevent pressure injuries, conventional practices rely on evaluation of the individual by a caregiver based on the Braden scale. Such practices, however, rely on the subjective evaluation by the caregiver of a number of equally weighted risk factors at a single point in time. Although the Braden scale is used for nearly 90% of pressure injury assessments, over 70% of pressure injuries developed by individuals were not predicted by the Braden scale.

Accordingly, a need exists for systems and methods that determine an objective pressure injury score and alter a treatment plan based on the same.

SUMMARY

According to some embodiments of the present disclosure, a system includes a plurality of sensors coupled to a person support apparatus configured to support a person on a support surface of the person support, at least one moisture sensor configured to sense a moisture level between the person and the support surface, and at least one computing device coupled to the plurality of sensors coupled to the person support apparatus and the at least one moisture sensor. The at least one computing device includes a processor and memory storing computer readable and executable instructions that, when executed by the processor, cause the computing device to receive data from the plurality of sensors coupled to the person support apparatus and the at least one moisture sensor, obtain data from an electronic medical record associated with the person supported by the person support apparatus, calculate a pressure injury score indicative of a likelihood that the person will develop a pressure injury based on the data from the plurality of sensors, the at least one moisture sensor, and the electronic medical record, and alter a treatment plan for the person based on the calculated pressure injury score.

According to some embodiments of the present disclosure, a method for altering a treatment plan for a person based on a pressure injury score indicative of a likelihood that the person will develop a pressure injury comprises receiving data from one or more sensors coupled to a person support apparatus indicative of a head angle of the person support apparatus; receiving data from one or more sensors coupled to the person support apparatus indicative of a mobility of a person supported on the person support apparatus; receiving data from a moisture sensor indicative of a moisture level between the person and the person support apparatus; receiving data regarding an age and a gender of the person from an electronic medical record associated with the person; calculating the pressure injury score by adjusting a baseline injury score for the facility based on the head angle of the person support apparatus, the mobility of the person, the moisture level, the age of the person, and the sex of the person; and altering the treatment plan for the person based on the calculated pressure injury score.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

Referring now to the illustrative examples in the drawings, wherein like numerals represent the same or similar elements throughout.

DETAILED DESCRIPTION

Figure 1:
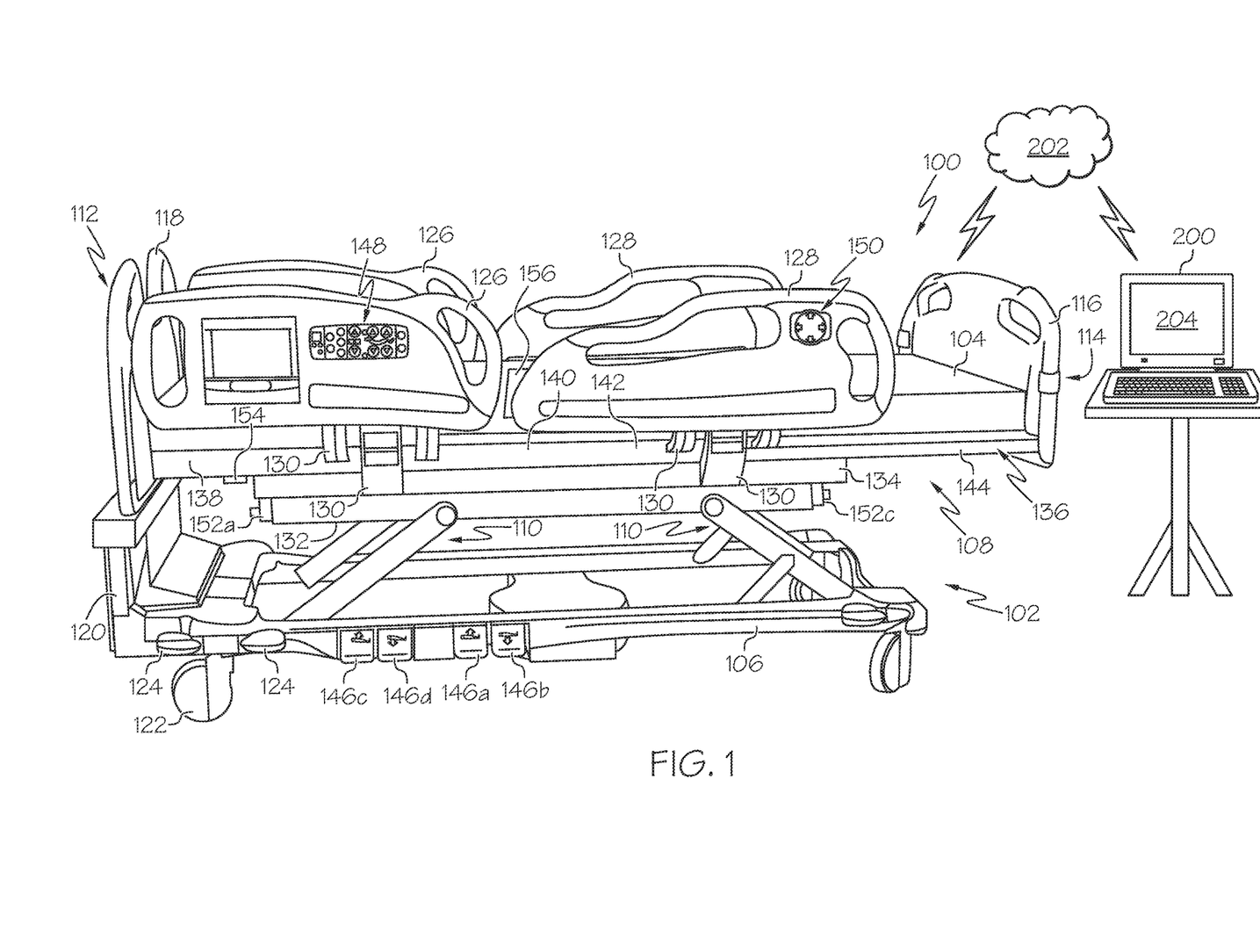
FIG. 1 is a perspective view of a person support apparatus according to one or more embodiments shown and described herein.

FIG. 1 generally depicts one embodiment of a person support apparatus for use in determining a pressure injury score. The person support apparatus includes a plurality of sensors that provide data that can be analyzed by a computing device to determine mobility of a person based on movement of the person on the person support apparatus. A moisture sensor is positioned between the person support apparatus and a person supported on the person support apparatus and provides data that can be analyzed by the computing device to determine a moisture level between the person and the person support apparatus. In embodiments, a computing device calculates a pressure injury score indicative of a likelihood that the person will develop a pressure injury based on data from the plurality of sensors, the moisture sensor, and data obtained from an electronic medical record associated with the person. Accordingly, the computing device can predict the occurrence of a pressure injury and alter a treatment plan for the person based on that prediction. Various embodiments of systems and methods for calculating a pressure injury score will be described in more detail herein with specific reference to the appended drawings.

A person support apparatus 100 including a frame 102 and a person support surface 104 is shown in FIG. 1. The frame 102 includes a base 106, an upper frame assembly 108, and a lift system 110 coupling the upper frame assembly 108 to the base 106. The lift system 110 is operable to raise, lower, and tilt the upper frame assembly 108 relative to the base 106. The person support apparatus 100 has a head end 112 and a foot end 114, and further includes a footboard 116 at the foot end 114 and a headboard 118 at the head end 112 of the person support apparatus 100. The headboard 118 is coupled to an upstanding portion 120 of the base 106 at the head end 112 of the person support apparatus 100. The footboard 116 is coupled to the upper frame assembly 108. The base 106 includes wheels or casters 122 that roll along a floor (not shown) as the person support apparatus 100 is moved from one location to another. A set of foot pedals 124 is coupled to the base 106 and is used to brake and release the casters 122.

As shown in FIG. 1, the person support apparatus 100 has four siderail assemblies coupled to the upper frame assembly 108. The four siderail assemblies include a pair of head siderail assemblies 126 (sometimes referred to as head rails) and a pair of foot siderail assemblies 128 (sometimes referred to as foot rails). Each of the siderail assemblies 126, 128 is movable between a raised position, as shown in FIG. 1, and a lowered position (not shown). Siderail assemblies 126, 128 are sometimes referred to herein as siderails 126, 128. Each siderail 126, 128 includes a linkage 130 coupled to the upper frame assembly 108 and configured to guide the siderails 126, 128 between the raised and lowered positions.

The upper frame assembly 108 includes a lift frame 132, a weigh frame 134 supported with respect to the lift frame 132, and a person support deck 136. The person support deck 136 is carried by the weigh frame 134 and engages a bottom surface of the person support surface 104. The person support deck 136 includes a head section 138, a seat section 140, a thigh section 142, and a foot section 144, as shown in FIG. 1. In various embodiments, sections 138, 142, and 144 are each movable relative to the weigh frame 134. For example, the head section 138 may pivotally raise and lower relative to the seat section 140, the foot section 144 may pivotally raise and lower relative to the thigh section 142, and the thigh section 142 may articulate relative to the seat section 140. Additionally, in some embodiments, the foot section 144 may extend and retract to change the overall length of the foot section 144 and, therefore, to change the overall length of the person support deck 136.

In the embodiment depicted in FIG. 1, the seat section 140 is fixed in position with respect to the weigh frame 134 as the person support deck 136 moves between its various positions including a horizontal position (shown in FIG. 1) and a chair position (not shown). In other embodiments, the seat section 140 also moves relative to the weigh frame 134, such as by pivoting and/or translating. In such embodiments, the thigh and foot sections 142, 144 may also translate along with the seat section 140. In the chair position, the head section 138 extends upwardly from the weigh frame 134 and the foot section 144 extends downwardly from the thigh section 142.

Additionally, the person support apparatus 100 includes four foot pedals 146a, 146b, 146c, 146d coupled to the base 106. In embodiments, the foot pedals may be used to raise and lower portions of the person support apparatus 100. For example, foot pedal 146a may be used to raise the upper frame assembly 108 relative to the base 106, the foot pedal 146b may be used to lower the upper frame assembly 108 relative to the base 106, the foot pedal 146c may be used to raise the head section 138 relative to the weigh frame 134, and the foot pedal 146d may be used to lower the head section 138 relative to the weigh frame 134. In other embodiments, one or more of the foot pedals may be omitted, or additional foot pedals may be included.

In embodiments, each siderail 126 includes a first user control panel 148 coupled to the outward side of the siderail 126 and each siderail 128 includes a second user control panel 150 coupled to the outward side of the siderail 128. The control panels 148, 150 include various buttons that may be used by a caregiver to control associated functions of the person support apparatus 100. For example, the first user control panel 148 may include buttons that are used to operate a motor to raise and lower the head section 138, buttons that are used to operate a motor to raise and lower the thigh section 142, and buttons that are used to operate motors to raise lower, and tilt the upper frame assembly 108 relative to the base 106. The second user control panel 150 may include buttons that are used to operate a motor to raise and lower the foot section 144 and buttons that are used to operate a motor to extend and retract the foot section 144.

In various embodiments, one or more components of the person support apparatus 100 are coupled to a computing device 200, which is configured to sense and/or collect information from the components coupled thereto, process the information, and perform one or more actions based on the information. The computing device 200 may additionally provide various resources to the person support apparatus 100. Resources include providing, for example, processing, storage, software, and information from other systems in the facility to the person support apparatus 100. In various embodiments, as will be described in greater detail below, the computing device 200 can calculate a pressure injury score based on information sensed or collected from various components of the person support apparatus 100, other sensors coupled to the computing device 200, and the electronic medical record (EMR) for the person. The components may be coupled wirelessly to the computing device 200, such as through a network 202, or the components may be coupled to the computing device 200 via wires. Accordingly, in some embodiments, one or more components of the person support apparatus 100 may include wireless communication circuitry, or be communicatively coupled to wireless communication circuitry incorporated into the person support apparatus 100 (not shown).

The computing device 200 may be any device having hardware (e.g., chipsets, processors, memory, etc.) for communicatively coupling with the network 202. Specifically, the computing device may be a mobile device, a desktop computing device, or a computing device incorporated into or attached to the person support apparatus 100, depending on the particular embodiment. For example, the computing device 200 may be a smart phone, a tablet device, an e-reader, a laptop computer, a desktop computer, or a computer associated with the person support apparatus 100. In various embodiments, the computing device 200 may be a device accessible by one or more caregivers, such as a computing device located at a nurses' station, in a doctor's office, or carried by the caregiver. In various embodiments, the computing device 200 can include an analytics engine, such as the analytics engine described in U.S. patent application Ser. No. 16/456,712, entitled "Patient Risk Assessment Based on data from Multiple Sources in a Healthcare Facility," filed on Jun. 28, 2019, the entire contents of which is incorporated by reference herein. For example, the analytics engine can perform any or all of the functions attributed herein to the computing device 200, including, without limitation, receiving data from sensors, calculating a pressure injury score, and altering a treatment plan for the person based on the calculated pressure injury score, as described herein.

Moreover, in various embodiments, the computing device 200 may be a digital safety net (DSN) platform, as described in greater detail in U.S. patent application Ser. No. 16/456,712. In such embodiments, the DSN platform may include an analytics engine, a Power over Ethernet (PoE) switch, a router or gateway that receives data from a multitude of sources as described herein and routes risk assessment information to a plurality of output devices such as graphical displays or mobile computing devices assigned to caregivers.

In various embodiments, the computing device 200 includes one or more non-transitory memory components, one or more processing devices, a display 204, a speaker, at least one input device, and network interface hardware. The one or more non-transitory memory components store computer readable and executable instructions that, when executed by the processor, cause the computing device 200 to perform one or more functions described herein. In particular, the one or more non-transitory memory components may store computer readable and executable instructions that, when executed by the processor, cause the computing device 200 to perform the functions of the various modules described hereinbelow, including but not limited to, analyzing data from one or more components of the person support apparatus 100, calculating a pressure injury score, causing a pressure injury score to be logged in an electronic medical record corresponding to the individual and/or altering a treatment plan for the individual. The at least one input device can include, by way of example and not limitation, a microphone, a keyboard, a touch screen, a mouse, or the like. The network interface hardware may depend on the particular embodiment, and may include the hardware to enable the computing device 200 to communicate via the network. The display can include any medium capable of transmitting an optical output such as, for example, a cathode ray tube, light emitting diodes, a liquid crystal display, a plasma display, or the like. Moreover, in some embodiments, the display is a touchscreen that, in addition to providing visual information, detects the presence and location of a tactile input upon a surface of or adjacent to the display. The computing device 200 may include additional or fewer components, depending on the particular embodiment. For example, in embodiments in which the computing device 200 is a smart phone, it may further include cellular network hardware and a microphone and not include a mouse, while in embodiments in which the computing device 200 is a desktop computing device, it may include a keyboard and a mouse and not include a touch screen.

In various embodiments, the computing device 200 is communicatively coupled to one or more input devices of the person support apparatus 100 that collect information indicative of mobility of a person or other factors that may influence the development of a pressure injury. For example, in various embodiments, the person support apparatus 100 may include sensors such as load cells 152a-152d, an angle sensor 154, a moisture sensor 156, or the like, that provide data to the computing device 200 which calculates a pressure injury score based on the received data. Various input devices and methods for calculating a pressure injury score will now be described.

In various embodiments, the person support apparatus 100 includes a number of load cells (collectively, load cells 152) positioned between the weigh frame 134 and the base 106. Each load cell is configured to produce a voltage or current signal indicative of a weight impressed on that load cell from the weigh frame 134 relative to the base 106. In the embodiment shown in FIG. 1, four load cells 152a, 152b, 152c, and 152d are positioned between the weigh frame 134 and the base 106; one at or proximate to each corner of the person support apparatus 100, although only two of the load cells 152a and 152c can be seen in FIG. 1. However, all four load cells 152a, 152b, 152c, and 152d are shown in FIG. 2.

Some of the structural components of the person support apparatus 100 will be designated hereinafter as "right," "left," "head," and "foot" from the reference point of an individual lying on the individual's back on the person support surface 104 with the individual's head oriented toward the head end 112 of the person support apparatus 100 and the individual's feet oriented toward the foot end 114 of the person support apparatus 100. For example, the weigh frame 134 illustrated in FIG. 2 includes a head end weigh frame member 134c mounted to one end of a right side weigh frame member 134a and at an opposite end to one end of a left side weigh frame member 134b. Opposite ends of the right side weigh frame member 134a and the left side weigh frame member 134b are mounted to a foot end weigh frame member 134d. A middle weigh frame member 134e is mounted at opposite ends to the right and left side weigh frame members 134a and 134b, respectively, between the head end and foot end weigh frame members 134c and 134d.

Figure 2:
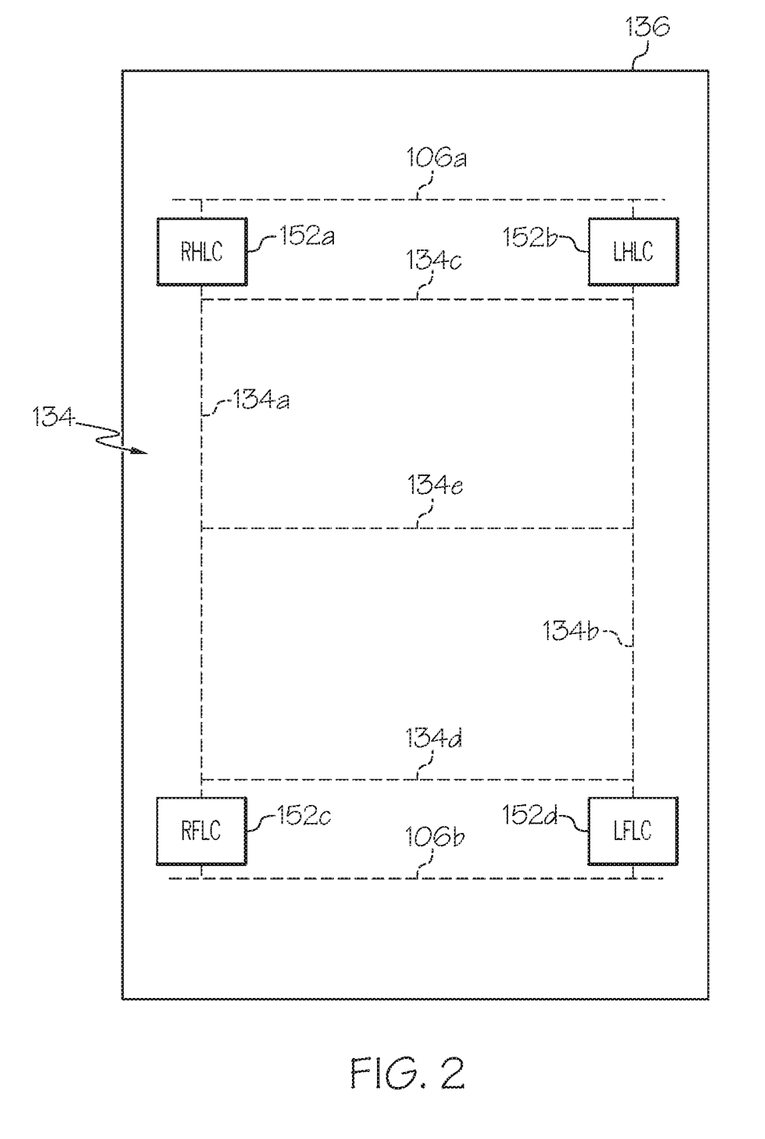
FIG. 2 is a block diagram illustrating locations of a number of load cells relative to the person support apparatus of FIG. 1.

A right head load cell (RHLC) 152a is illustratively positioned near the right head end of the person support apparatus 100 between a base support frame 106a secured to the base 106 near the head end 112 and the junction of the head end weigh frame member 134c and the right side weigh frame member 134a, as shown in the block diagram of FIG. 2. A left head load cell (LHLC) 152b is illustratively positioned near the left head end of the person support apparatus 100 between the base support frame 106a and the junction of the head end weigh frame member 134c and the left side weigh frame member 134b. A right foot load cell (RFLC) 152c is illustratively positioned near the right foot end of the person support apparatus 100 between a base support frame 106b secured to the base 106 near the foot end 114 of the person support apparatus 100 and the junction of the foot end weigh frame member 134d and the right side weigh frame member 134a. A left foot load cell (LFLC) 152d is illustratively positioned near the left foot end of the person support apparatus 100 between the base support frame 106b and the junction of the foot end weigh frame member 134d and the left side weigh frame member 134b. In the embodiment depicted in FIG. 2, the four corners of the person support deck 136 are shown extending beyond the four corners of the weigh frame 134, and hence beyond the positions of the four load cells 152a-152d.

In the illustrated embodiment, each of the load cells 152a-152d are weight sensors comprising resistive strain gauges coupled to a deflectable block (not shown), and structurally couple the weigh frame 134 to the base 106. It will be appreciated, however, that other weight detection devices may be used. Such devices may include, but are not limited to, linear variable displacement transducers (LVDTS) and/or other weight detection devices operable in accordance with known capacitive, inductive, or other physical principles. Moreover, alternative person support apparatuses can be employed, including but not limited to, air mattresses or the like.

In various embodiments, the load cells 152a-152d generate a signal which is transmitted to the computing device 200. In other words, the load cells 152a-152d generate load cell data that is transmitted to the computing device 200. As will be described in greater detail below, the computing device 200 receives the load cell data and, using a load pattern analysis module, may analyze the load cell data (e.g., waveforms) received from the load cells 152a-152d in order to detect a mobility level for a person supported on the person support apparatus 100. For example, the load pattern analysis module may determine that a particular waveform is indicative of a possible patient turn, a person changing positions on the person support apparatus, a general degree of movement within the person support apparatus, or the like. The term "a load pattern analysis module" may also be referred to herein as "a motion assessment module."

Returning to FIG. 1, in various embodiments, the person support apparatus 100 further includes an angle sensor 154 coupled to the computing device 200. The angle sensor 154 may be, for example, an accelerometer that operates as part of a head of bed angle monitoring system, such as the head of bed angle monitoring system described in U.S. Patent Application Publication No. 2011/0083271 filed on Sep. 30, 2010, and entitled "Head of bed angle mounting, calibration, and monitoring system," the entire contents of which is hereby incorporated by reference. The angle sensor 154 detects an angle of the head of the bed. In embodiments, the angle sensor 154 is positioned on the back side (e.g., a side opposite the person support surface) of the articulating head section 138 of the person support deck 136 such that the angular position of the angle sensor 154 follows the angular position of the head section 138 through the full range of articulation. However, it is contemplated that the angle sensor 154 may be coupled to another suitable portion of the head section 138, such as, for example, a frame member, a deck panel, a portion of the mattress, or a siderail 126 that moves along with the head section 138. The angle sensor 154 is oriented such that a measurement axis of the angle sensor 154 enables the angle sensor 154 to measure dynamic acceleration along the measurement axis over time. In embodiments, the angle sensor 154 may further measure static acceleration. The static acceleration measurement represents the orientation of the measurement axis of the angle sensor 154 relative to the force of gravity, which is vertical to the true horizon.

As the head section 138 is moved from one position to a different position, the measurement axis experiences sufficient changes in gravitational force to resolve the head of bed angle degree changes throughout the range of movement within a specified margin of error. In embodiments, the output generated by the angle sensor 154 is transmitted to the computing device 200, which processes the output, including, for example, amplifying the output, and using the output to calculate a pressure injury score.

Still referring to FIG. 1, various embodiments further include at least one moisture sensor 156 coupled to the computing device 200. The moisture sensor 156 may be, for example, a moisture sensor that operates as part of a moisture detection system, such as the moisture detection system described in U.S. Pat. No. 8,826,473 filed on Jul. 19, 2011, and entitled "Moisture detection system," the entire contents of which is hereby incorporated by reference. In embodiments, the moisture sensor 156 detects a moisture level between a person supported on the person support surface 104 and the person support surface 104. The moisture sensor 156 may be, by way of example and not limitation, a capacitive sensor, a resistive sensor, or a thermally conductive sensor. It should be appreciated that other types of moisture sensors may be employed.

The moisture sensor 156 of various embodiments may be external to the person support apparatus 100, such as a sensor disposed on top of the person support surface 104, or it may be integrated into the person support apparatus 100, such as positioned between a core layer and a ticking of the person support surface 104. Moreover, the moisture sensor 156 may be positioned at any one or more locations along the length and width of the person support apparatus 100. In various embodiments, the moisture sensor 156 is positioned at a seat area of the person support apparatus 100 such that the moisture sensor 156 can detect, for example, incontinence.

In some embodiments, the moisture sensor 156 may be coupled to a moisture detection sheet (not shown). The moisture detection sheet may be made of any suitable material, including organic, inorganic, or synthetic materials or fabrics. In some embodiments, fibers of the moisture detection sheet may serve as moisture sensors 156. In embodiments including a moisture detection sheet, the moisture detection sheet may absorb moisture between the person supported on the person support apparatus 100 and the person support surface and/or redistribute and direct the moisture to the moisture sensor 156.

As described above, the moisture sensor 156 is coupled to the computing device 200 and conveys data to the computing device 200 in the form of electrical signals indicative of the moisture level between the person supported on the person support apparatus 100 and the person support surface. Communication between the moisture sensor 156 and the computing device 200 may be wired or wireless. In embodiments, the moisture sensor 156 may transmit raw data regarding the moisture level to the computing device 200, while in other embodiments, the moisture sensor 156 may include components to enable the moisture sensor 156 to determine a moisture level and transmit the moisture level to the computing device 200. The computing device 200 of various embodiments may utilize the moisture level to calculate the pressure injury score.

Additional sensors coupled to the computing device 200 may further be used to collect data for use in calculating a pressure injury score. For example, a physiological monitor 158 (shown in FIG. 3) for sensing data regarding a blood pressure, a temperature, or another physiological parameter, including without limitation, a heart rate, a respiration rate, a blood oxygen saturation level, of the person may be coupled to the computing device 200. Such physiological monitors may be standalone monitors, or may be integrated into the person support apparatus 100, as described in U.S. Patent Application Publication No. 2014/0323816, entitled "Systems for Patient Support, Monitoring and Treatment," filed on Jun. 9, 2014, the entire contents of which is hereby incorporated by reference. As with the other sensors and monitors described herein, the physiological monitor 158 are communicatively coupled to the computing device 200 via wires or wirelessly, and may transmit data to the computing device 200 regarding one or more physiological parameters for the person supported by the person support apparatus 100. In embodiments, raw data may be transmitted to the computing device 200 by the physiological monitor 158, or the physiological monitor 158 may transmit final calculations regarding the physiological parameter to the computing device 200. In some particular embodiments, the physiological parameter may be saved into the EMR for the person along with a time stamp indicative of the time that the physiological parameter was measured.

Figure 3:
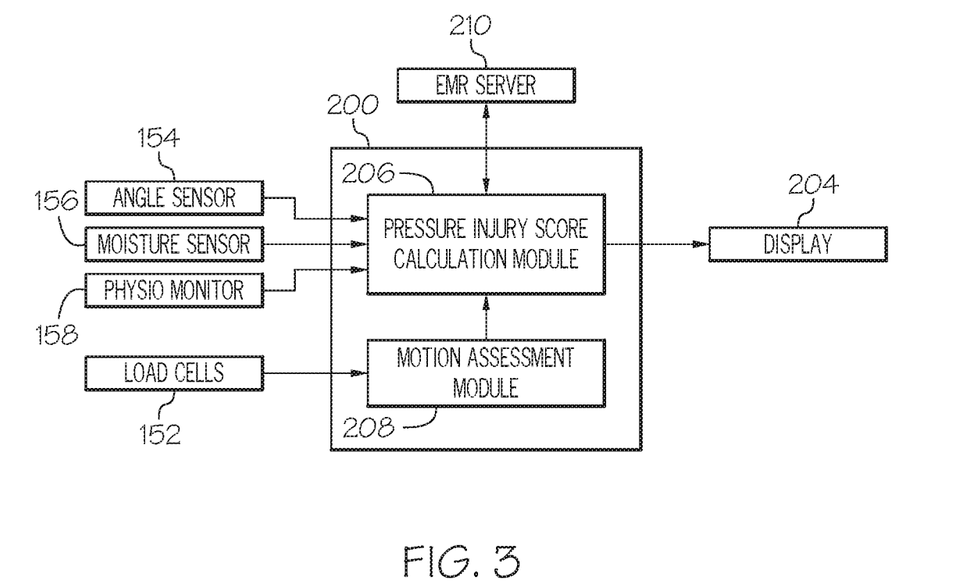
FIG. 3 is a block diagram illustrating an example computing device for calculating a pressure injury score for an individual according to one or more embodiments shown and described herein.

FIG. 3 is a schematic block diagram illustrating components of the computing device 200. In various embodiments, the computing device 200 includes a pressure injury score calculation module 206 and a motion assessment module 208. It is contemplated that other modules may be included, depending on the particular embodiment.

In various embodiments, the pressure injury score calculation module 206 is adapted to calculate a pressure injury score indicative of a likelihood that the person supported on the person support apparatus 100 will develop a pressure injury. In particular, the pressure injury score calculation module 206 is adapted to analyze the data from the load cells 152 (and/or the motion assessment module 208), angle sensor 154, moisture sensor 156, physiological monitor 158, and combinations thereof to objectively determine whether the person is likely to develop a pressure injury. For example, in various embodiments, the pressure injury score calculation module 206 may utilize a non-linear regression model which bounds a probability of developing a pressure injury between 0 and 1 to determine whether the person is likely to develop a pressure injury. In the various embodiments described herein, the computing device 200 may provide a notification regarding the pressure injury score to a caregiver via one of the user interfaces described herein, and/or cause a treatment plan for the person to be altered.

The computing device 200 may include circuitry (not shown) for processing the raw signal generated by the load cells 152*a*-152*d*, the angle sensor 154, the moisture sensor 156, and/or the physiological monitor 158, such as at least one pre-amplifier, at least one filter, and an analog-to-digital (A/D) converter. The filter may be a band-pass or a low-pass filter. The low-passed data may be digitized at an appropriate sampling rate (e.g., 10 Hz) and stored in memory. After the A/D converter converts the amplified and filtered signal, it is passed to the motion assessment module 208 for assessment of the mobility and/or activity level of the person and/or to the pressure injury score calculation module 206 for calculation of the pressure injury score.

The motion assessment module 208 may be used to assess a person's activity and/or mobility based on at least information from the load cells 152. As used herein, the term "mobility" refers to a person's ability to offload themselves (e.g., egress), or make relatively minor changes in the position of their body, or an extremity thereof, while they are supported by a person support apparatus, without assistance from another person. Some examples of changes in position that are representative of a person's mobility include rolling from one's side onto the back or front, rolling from the back or front onto one's side, lifting or turning the head, raising or lowering an arm or leg, bending a knee or elbow, and flexing a foot or wrist.

In some embodiments, a person's motion may be considered separately from a person's activity level, as is described in U.S. Pat. No. 9,295,600, entitled "Person support apparatus with activity and mobility sensing," filed on Apr. 10, 2012, the entire contents of which is hereby incorporated by reference.

In various embodiments, the motion assessment module 208 receives one or more inputs, such as from the load cells 152. It is contemplated that other inputs may be received by the motion assessment module 208 and used to calculate the mobility and/or activity score, such as inputs regarding a pressure of one or more air bladders forming or supporting the person support surface. In various embodiments, the mobility score is a function of the changes in magnitude of sensor inputs received by the load cells 152 over a time interval defined for mobility monitoring. In embodiments, the motion assessment module 208 can analyze the data, and particularly, the number and frequency of changes in the magnitude of inputs over the defined mobility monitoring time interval, in order to focus on sensor inputs indicative of mobility and/or activity rather than physiological signals and, in some embodiments, activity. Other factors that can affect the motion assessment include person's weight, body type, or other factors. Activity and mobility can also change as a function of time as the factors influencing those scores change.

The mobility or activity scores may be derived, for example, by mapping the results of the analysis to predetermined or threshold values. The predetermined values and corresponding mobility and activity scores may be stored in computer memory, such as in the form of a lookup table. Additional details on analysis of the data and derivation of the mobility score are provided in U.S. Pat. No. 9,295,600.

In various embodiments, the mobility score is communicated from the motion assessment module 208 to the pressure injury score calculation module 206 and may be used by the pressure injury score calculation module 206 to calculate a pressure injury score. In particular, a higher mobility score (corresponding to a lower mobility) may indicate a higher risk of developing a pressure injury and a lower mobility score may indicate a higher degree of mobility and, thus, a lower risk of developing a pressure injury. For example, a mobility score of "10" may indicate that a person is completely immobile, i.e., unable to make even slight changes in the position of the body or an extremity without assistance. A mobility score of "6" may indicate that a person's mobility is very limited, but the person is not completely immobile, and can make occasional slight changes in position of the body or extremity, but is unable to make frequent or significant changes without help. A mobility score of "3" may indicate that the person's mobility may be only slightly limited and that the person is able to make frequent, though slight, changes in position of the body or extremity without assistance. A mobility score of "0" may indicate that the person has no limitations relating to mobility, and can make frequent and major changes in position without assistance. Accordingly, an assessment of a person's mobility can include an assessment of a change in position (e.g., whether the person moved from laying down to sitting up, or merely raised their head) and an assessment of the frequency of such changes in position (e.g., how often the person makes even minor changes in position).

In various embodiments, an activity score is communicated from the motion assessment module 208 to the pressure injury score calculation module 206 and may be used by the pressure injury score calculation module 206 to calculate a pressure injury score. In particular, a higher activity score (corresponding to a lower activity) may indicate a higher risk of developing a pressure injury and a lower activity score may indicate a higher degree of activity and, thus, a lower risk of developing a pressure injury. For example, an activity score of "10" may indicate that a person did not exit the bed at all during a predetermined time period. An activity score of "6" may indicate that a person's activity is very limited, but the person very occasionally exits and re-enters the bed, such as a couple of times per day. An activity score of "3" may indicate that the person's activity may be only slightly limited and that the person is able to frequently exit and re-enter the bed without assistance. An activity score of "0" may indicate that the person has no limitations relating to activity, and can frequently exit and re-enter the bed without assistance. Accordingly, an assessment of a person's activity can include an assessment of a number of times the person exited and re-entered the bed.

Figure 4:
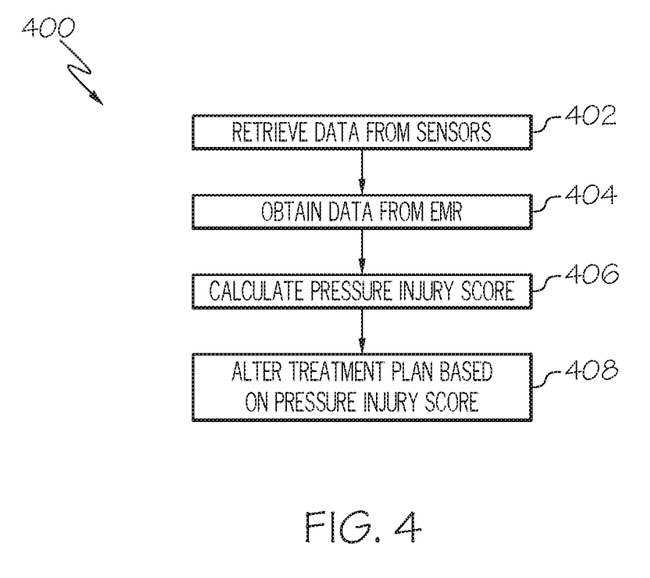
FIG. 4 is a block diagram of an example method for altering a treatment plan based on a calculated pressure injury score according to one or more embodiments shown and described herein.

FIG. 4 depicts an example method 400 of altering a treatment plan based on a calculated pressure injury score. The method 400 may be performed, for example, by the pressure injury score calculation module 206 on the computing device 200. As described herein, the method begins by receiving data from various sensors (step 402). The various sensors may include, by way of example and not limitation, the angle sensor 154, the load cells 152, the moisture sensor 156, physiological monitors 158, and the like.

Although in embodiments, the computing device 200 is described as receiving or collecting information from the angle sensor 154, the load cells 152a-152d, the moisture sensor 156, and the physiological monitor 158, it is contemplated that any number of separate computing devices may be employed. For example, the angle sensor 154 may be communicatively coupled to one computing device while the load cells 152a-152d are communicatively coupled to a second computing device including the motion assessment module 208, with each computing device performing analysis on the data it receives. For example, the computing device communicatively coupled to the load cells 152a-152d, and specifically, the motion assessment module 208, may perform a mobility analysis for the person to determine a motion level based on movement of the person on the person support apparatus 100. Moreover, it should be understood that additional and/or alternative inputs may be employed depending on the particular embodiment. For example, in some embodiments, the person support surface 104 may include one or more pressure sensors that can detect movement of a patient based on a redistribution of pressure over the person support surface 104. Such systems may be used for predicting egress of an individual from the person support apparatus 100, and the data may be additionally analyzed by the motion assessment module to determine motion of the person or otherwise calculate the pressure injury score. Additional details on systems for use in predicting egress may be found in U.S. Pat. No. 9,761,109, entitled "Occupant Egress Prediction Systems, Methods, and Devices," the entire contents of which is hereby incorporated by reference.

Next, at step 404, data from person's electronic medical record (EMR) is obtained. For example, the pressure injury score calculation module 206 may obtain information regarding previous clinical events stored in the person's EMR, such as may be stored on an EMR server 210. Accordingly, as depicted in FIG. 3, the pressure injury score calculation module 206 may be communicatively coupled to an EMR server 210 storing the EMR for the person. However, it is contemplated that, in some embodiments, the EMR may be stored on the computing device 200. Regardless of where it is stored, the EMR may provide to the computing device 200 information such as, by way of example and not limitation, data regarding previous or existing pressure injuries, an age of the person, the sex of the person, medication administered to the person, an amount of time the person was in an operating room, an indication that the person has diabetes, and nutritional information related to the person. Additionally, as described above, one or more physiological parameters for the person may be stored in the EMR and provided to the computing device 200.

Returning to FIG. 4, at step 406, the pressure injury score is calculated. In various embodiments, the pressure injury score calculation module 206 calculates a pressure injury score by adjusting a baseline pressure injury value upwards or downwards, depending on the data received from the various sensors. The baseline pressure injury value may be, by way of example and not limitation, a facility baseline value that is determined based on the likelihood that a person being treated at a particular facility will develop a pressure injury. For example, the facility baseline value may be a value of from 0 to 1, where 0 indicates that the facility very rarely has persons develop pressure injuries and 1 indicates that the facility very frequently has persons develop pressure injuries. In some particular embodiments, the baseline pressure injury score may be the percentage of individuals that develop a pressure injury in the facility, expressed as a decimal.

In the embodiments described herein, the pressure injury score calculation module 206 may modify the baseline pressure injury value by weighting the data received from the various sensors described herein. The weighting may be determined according to an importance to the particular factor in the development of a pressure injury or in the prevention of a pressure injury. As but one example, the mobility score received from the motion assessment module 208 may be accorded the greatest weight (e.g., 2-5 times greater than any other factor), while an indication that the person supported by the person support apparatus 100 is male may be weighted less heavily. The weighting of the factors may depend on, for example, the amount of data received by the pressure injury score calculation module 206 and the particular non-linear regression employed. It is contemplated that any suitable non-linear regression may be employed to calculate the pressure injury score, provided that the model bounds the probability between 0 and 1.

The influence of various factors, the sensor(s) from which the data pertaining to each factor is obtained, and example weighting for each factor are provided in Table 1.

TABLE 1

Effects of Various Factors on Pressure Injury Score Calculation

| Factor | Data provided by | Effect on Pressure Injury Score | Weight |
|---|---|---|---|
| Restricted mobility | Load cells and/or pressure sensors | Increase | 2-5x |
| Limited mobility | Load cells and/or pressure sensors | Increase | 2-5x |
| Head of bed angle | Angle sensor | Increase | |
| Air Surface | EMR | Decrease | |
| Time incontinent | Moisture sensor | Increase | 1.2-1.5x for each 15 minutes of exposure |
| Person has an existing pressure injury | EMR | Increase | 2-3x |
| Age | EMR | Increase | 1.002-1.01x for each year of age |
| Sex of person | EMR | Increase | 1.3-1.4x for male |
| Diabetes | EMR | Increase | 1.3-2.5x when condition is present |
| Time in the Operating Room | EMR | Increase with increasing time | |
| Time in the Emergency Room | EMR | Increase with increasing time | |
| Vasopressors | EMR | Increase | 1.5-2x when vasopressors have been administered |
| Time in the ICU | EMR | Increase with increasing time | 1.2-2x |

The baseline pressure injury value is adjusted up or down based on the weighted factors, and the result, in various embodiments, is the pressure injury score. The pressure injury score may be stored in the person's EMR and updated at particular periods of time, such as every 4 hours, every 6 hours, every 8 hours, every 12 hours, every 24 hours, or every 48 hours, for example. In embodiments, the pressure injury score may be a value between 0 and 1, where 0 indicates that person is very unlikely to develop a pressure injury and 1 indicates that the person is certain to develop pressure injuries.

By way of example, in various embodiments, a baseline pressure injury score is 0.01 for an individual that is within a demographic and possesses the average characteristics for an individual treated at a particular facility (e.g., average age, average weight, and no comorbidities that would increase the risk of a pressure injury). When an individual is admitted, a new pressure injury risk score may be calculated based on their characteristics which may increase that risk. For an individual that has an average age and average weight for that facility, the pressure injury score remains at 0.01. However, when the individual is a male, the pressure injury score increases by a factor of 1.4, giving a pressure injury score of 0.014. An existing pressure injury was recorded in the individual's EMR, increasing the risk by a factor of 3, increasing the score to 0.042. Accordingly, the individual's pressure injury score at admission was 0.042.

Consider that, during the time the individual is in the facility, the person support apparatus determines that the individual is only able to make small shifts in his weight (e.g., diminished mobility), increasing his score from 0.042 by a factor of 4 to 0.168. Then, the individual has an incontinence event, which increases the score by a factor of 1.2, giving a pressure injury score of 0.2016. After a few days in the facility, the individual is admitted to the intensive care unit (ICU) (increasing the pressure injury score by a factor of 2) and administered vasopressors (further increasing the pressure injury score by a factor of 1.5), and his pressure injury score increases to 0.6048. Based on the progression of the pressure injury score of the individual during his time in the facility, his treatment plan is not adjusted based on the pressure injury score at admission (0.042), but the treatment plan is subsequently modified as it is determined that he has limited mobility based on the adjusted score. Specifically, following the individual's admission to the ICU, the treatment plan may be adjusted based on the calculated pressure injury score, as it has increased from medium risk to high risk.

In addition to calculating and causing the pressure injury score to be stored in the person's EMR, in various embodiments, the computing device 200 alters a treatment plan for the person based on the calculated pressure injury score (step 408). The treatment plan may be altered, for example, by providing suggested treatment steps to a caregiver via the display 204 or via a mobile computing device carried or otherwise accessed by the caregiver. Additionally or alternatively, the treatment plan may be altered by transmitting a reminder, alert, or notification to the caregiver.

In some embodiments, alterations to the treatment plan can include turning the person or increasing the frequency with which the person is turned, recommending that an incontinence pad be positioned or replaced between the person and the support surface, recommending a nutrition consult for the person, replacing or altering a support surface on which the person is disposed, or combinations thereof. In some embodiments, alterations to the treatment plan may include providing reminders regarding the angle of the head of the bed, ordering lateral rotation therapy, adjusting a blower coupled to the person support surface, providing a skin care treatment, or the like. As will be appreciated, the particular alterations to the treatment plan may depend on the specific pressure injury score. For example, if the calculated pressure injury score is between 0 and 0.10 (on a scale between 0 and 1), the score may be saved into the EMR, but the treatment plan may not be altered to include preventative measures. If the calculated pressure injury score is greater than 0.10 and less than or equal to 0.33, the treatment plan may be altered by providing a turn reminder if the person is not mobile (based on the motion assessment score) and/or recommending that the incontinence pad be replaced. If the calculated pressure injury score is greater than 0.33 and less than or equal to 0.55, the treatment plan may be altered by providing a turn reminder if the person is not mobile (based on the motion assessment score), recommending that the incontinence pad be replaced, recommending a nutrition consult for the person, and/or adjusting the firmness/softness of the support surface to reduce or redistribute pressure on one or more areas of the person's body. If the calculated pressure injury score is greater than 0.55 and less than or equal to 1.0, the treatment plan may be altered by providing a turn reminder if the person is not mobile (based on the motion assessment score), recommending that the incontinence pad be replaced, recommending a nutrition consult for the person, adjusting the firmness/softness of the support surface to reduce or redistribute pressure on one or more areas of the person's body, and/or replacing the person support apparatus with a different person support apparatus, such as a person support apparatus including a therapy surface.

As described above, in various embodiments, altering the treatment plan may include providing a suggestion, alert, or notification to a caregiver, such as through a status board, a graphical room station, or a mobile device assigned to a caregiver. Such devices may be associated with a nurse call system, such as the NAVICARE® Nurse Call system available from Hill-Rom Company, Inc. of Batesville, Ind. Additional details of suitable nurse call systems, status boards, graphical room stations, and mobile devices can be found in U.S. Pat. Nos. 8,779,924; 7,746,218; 7,538,659; 7,319,386; 7,242,308; 6,897,780; 6,147,592; 5,838,223; 5,699,038; and 5,561,412 and in U.S. Patent Application Publication Nos. 2009/0217080; 2009/0214009; 2009/0212956; 2009/0212925; and 2019/0108908, each of which is hereby incorporated by reference herein in its entirety. In some embodiments, altering the treatment plan may further include automatically placing an order for one or more items to be provided to the person. For example, if the calculated pressure injury score is greater than 0.10 and less than or equal to 0.33, the treatment plan may be altered by the computing device 200 ordering an incontinence pad to be delivered to the person's room. Other alterations to the treatment plan are contemplated, based on the particular embodiment and facility.

Although the method is described as being performed by a computing device, it is contemplated that in some embodiments, more than one computing device or server communicatively coupled to the network 202 may perform one or more of the steps in the method. Accordingly, it should be understood that various facility information systems (e.g., the NaviCare® system from Hill-Rom, EMR systems, the Smart Connect® system from Hill-Rom, and the SmartSync® system from Hill-Rom) may communicate with one another in the various embodiments described herein to perform the functions described. Additionally, it is contemplated that the computing device 200 may receive health-related data from network-enabled products in the room and other facility information systems in addition to the data described hereinabove for use in calculating the pressure injury score.

In some embodiments, feedback regarding whether the person later developed a pressure injury (e.g., such as may be included in the person's EMR) may be received by the pressure injury score calculation module 206 and used to improve the calculation method (e.g., non-linear model) over time via machine learning techniques.

Moreover, in some embodiments, the computing device 200, and specifically the pressure injury score calculation module 206, may compare treatment plans for different individuals and identify caregivers or treatment practices that produce a decreased risk of pressure injuries, such as fewer overall pressure injuries or less severe pressure injuries. Identification of treatment practices that result in lower pressure injury scores may be used to alter treatment plans for other individuals, as described above.

Accordingly, various embodiments described herein the system receives data from various sensors and other sources and calculates an objective pressure injury score indicative of a likelihood that a person will develop a pressure injury. The pressure injury score may be used to alter a treatment plan for the individual based on the pressure injury score, thereby reducing the occurrence of pressure injuries for persons in various healthcare facilities.

Many additional embodiments other than those described above are possible and still included in the spirit and scope of the claims defining the embodiments described herein. For example, although various combinations of features of a system for altering a treatment plan based on a calculated pressure injury score have been shown and described, it is contemplated that these features may be combined in other ways described in detail or illustrated in the accompanying figures.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A system comprising:
   a plurality of load sensors coupled to a person support apparatus configured to support a person on a support surface of the person support apparatus configured to sense a mobility of the person on the person support apparatus;
   at least one moisture sensor positioned between the person and the support surface configured to sense a moisture level between the person and the support surface; and
   at least one computing device coupled to the plurality of load sensors and the at least one moisture sensor, the at least one computing device comprising a processor and memory storing computer readable and executable instructions that, when executed by the processor, cause the computing device to:
   receive data from the plurality of load sensors coupled to the person support apparatus and the at least one moisture sensor;
   calculate, using a load pattern analysis module, a mobility score indicative of a mobility of the person based on the data from the plurality of load sensors, the mobility score being a function of changes in magnitude of sensor inputs received by the plurality of load sensors over a time interval defined for mobility monitoring;
   obtain data from an electronic medical record associated with the person supported by the person support apparatus;
   calculate a pressure injury score indicative of a likelihood that the person will develop a pressure injury based on the mobility score, the at least one moisture sensor, and the electronic medical record; and
   alter a treatment plan for the person based on the calculated pressure injury score,
   wherein calculating the pressure injury score comprises adjusting a healthcare facility baseline value based on the data from the plurality of sensors, the at least one moisture sensor, and the electronic medical record.

2. The system of claim 1, wherein the data obtained from the electronic medical record is selected from the group consisting of data regarding previous or existing pressure injuries, an age of the person, the sex of the person, medication administered to the person, an amount of time the person was in an operating room, an indication that the person has diabetes, a frequency of patient turns, and nutritional information related to the person.

3. The system of claim 1, wherein calculating the pressure injury score comprises weighting the mobility of the person in the calculation greater than other received data.

4. The system of claim 1, further comprising:
   a monitor for sensing data regarding a blood pressure or a temperature of the person;
   wherein the executable instructions, when executed by the processor, further cause the computing device to receive the data from the monitor, and calculate the pressure injury score based on the blood pressure or the temperature.

5. The system of claim 1, further comprising an angle sensor coupled to a head end of the person support apparatus, wherein the executable instructions, when executed by the processor, further cause the computing device to receive data from the angle sensor regarding a head angle of a bed.

6. The system of claim 1, further comprising:
   a mobile computing device communicatively coupled to the computing device;
   wherein altering the treatment plan comprises transmitting a turn reminder to the mobile computing device indicative that the person should be turned on the person support apparatus.

7. The system of claim 1, wherein altering the treatment plan comprises providing a recommendation that an incontinence pad positioned between the person and the support surface be replaced.

8. The system of claim 1, wherein altering the treatment plan comprises providing a recommendation for a nutrition consult for the person.

9. The system of claim 1, wherein altering the treatment plan comprises causing the person support apparatus to be replaced with a different person support apparatus.

* * * * *